(12) United States Patent
Rowland et al.

(10) Patent No.: US 7,339,172 B2
(45) Date of Patent: Mar. 4, 2008

(54) PORTABLE COMPTON GAMMA-RAY DETECTION SYSTEM

(75) Inventors: Mark S. Rowland, Alamo, CA (US); Mark E. Oldaker, Pleasanton, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 102 days.

(21) Appl. No.: 11/327,722

(22) Filed: Jan. 5, 2006

(65) Prior Publication Data
US 2007/0152160 A1 Jul. 5, 2007

(51) Int. Cl.
G01T 1/161 (2006.01)

(52) U.S. Cl. .................. 250/363.02; 250/370.1

(58) Field of Classification Search .......... 250/363.02, 250/370.1
See application file for complete search history.

(56) References Cited

U.S. PATENT DOCUMENTS

| | | | |
|---|---|---|---|
| 4,124,804 A | 11/1978 | Mirell | |
| 4,495,636 A | 1/1985 | Jacobs et al. | |
| 5,175,434 A | 12/1992 | Engdahl | |
| 5,665,971 A | 9/1997 | Chen et al. | |
| 5,821,541 A | 10/1998 | Tumer | |
| 6,175,120 B1 * | 1/2001 | McGregor et al. | 250/370.13 |
| 6,207,957 B1 * | 3/2001 | Kammeraad et al. | 250/370.1 |
| 6,528,795 B2 | 3/2003 | Kurfess et al. | |
| 2003/0136916 A1 * | 7/2003 | Kearfott et al. | 250/393 |
| 2003/0161526 A1 | 8/2003 | Jupiter et al. | |
| 2004/0000645 A1 * | 1/2004 | Ramsden et al. | 250/361 R |
| 2004/0164250 A1 * | 8/2004 | Cork et al. | 250/390.06 |
| 2005/0105665 A1 | 5/2005 | Grodzins et al. | |

OTHER PUBLICATIONS

No Author, Radiation Detection on the Front Lines, Science & Technology Review, Sep. 2004, 6 pages.

* cited by examiner

Primary Examiner—Dave Porta
Assistant Examiner—Jessica L Eley
(74) Attorney, Agent, or Firm—Eddie E. Scott; John H. Lee

(57) ABSTRACT

A Compton scattered gamma-ray detector system. The system comprises a gamma-ray spectrometer and an annular array of individual scintillators. The scintillators are positioned so that they are arrayed around the gamma-ray spectrometer. The annular array of individual scintillators includes a first scintillator. A radiation shield is positioned around the first scintillator. A multi-channel analyzer is operatively connected to the gamma-ray spectrometer and the annular array of individual scintillators.

5 Claims, 3 Drawing Sheets

PORTABLE COMPTON GAMMA-RAY DETECTION SYSTEM

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to gamma-ray detection and more particularly to a portable Compton gamma-ray detection system.

2. State of Technology

United States Patent Application No. 2003/0161526 by Clyde P. Jupiter and Nenad N. Kondic for a non-invasive stationary system for three-dimensional imaging of density fields using periodic flux modulation of compton-scattered gammas, published Aug. 28, 2003 provides the following state of technology information, "There is a recognized and growing need for improved capability to 'see' inside closed boundaries of objects and for accurate measurement of their internal characteristics. For instance, inspection devices are needed to examine baggage and containers to enhance security and search for contraband at airports, government facilities, public buildings, and other possible targets of terrorism. Inspection devices can be installed at check points to scan baggage and other types of containers so that their contents can be characterized and inspected for contraband such as explosives, weapons, drugs and other illicit substances. Non-invasive inspection devices have also become an important tool for on-line monitoring of characteristics of materials undergoing industrial processing within tanks and pipes." The disclosure of United States Patent Application No. 2003/0161526 for a non-invasive stationary system for three-dimensional imaging of density fields using periodic flux modulation of Compton-scattered gammas is incorporated herein by reference.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The University of California has operated the Lawrence Livermore National Laboratory continuously since the laboratory's inception in 1952 and the Laboratory draws on 50+ years of experience in all aspects of nuclear weapons to address the challenge of nuclear nonproliferation by rogue nations or terrorist groups. Because the materials required for nuclear weapons do not occur naturally, the best way to prevent nuclear proliferation or terrorism is to protect and control nuclear materials. This requires the latest technology in radiation detection.

The article "Radiation Detection on the Front Lines" in the September 2004 issue of *Science and Technology Review* states, "Livermore scientists and engineers have made significant advancements in radiation detection equipment. Isotopes are now more easily distinguishable, reducing the confusion between threatening and nonthreatening sources. 'We don't know exactly how a terrorist will build a device,' says Labov. 'But now we have more sophisticated instruments that have better spectral resolution. These instruments help us to identify common and legitimate radioactive materials, which increases our sensitivity to possible threats.' Specialized integrated circuits and microelectronics, improved computer codes, and advancements in detector materials have made these instruments possible . . . . Recent advances in semiconductor detector manufacturing and electronics enable high-sensitivity, high-spatial-resolution gamma-ray detectors. Gamma-ray tracking algorithms, which accurately determine of the path of gamma rays within the detector, will ultimately allow us to deduce the incident direction of gamma rays without the use of collimators. This so-called Compton camera concept can be realized in compact and potentially portable systems, which provide omnidirectional sensitivity. We are pursuing two different versions of this concept: a single, full-volume system and a 'hybrid' system built of two different detector materials). Both systems provide excellent isotope identification. However, the single, full-volume system is characterized by its omnidirectional imaging while the hybrid system is characterized by its angular resolution and high sensitivity for a wide range of nuclear materials."

The present invention provides a Compton scattered gamma-ray detector system. The system comprises a gamma-ray spectrometer and an annular array of individual scintillators. The scintillators are positioned so that they are arrayed around the gamma-ray spectrometer. The annular array of individual scintillators includes a first scintillator. A radiation shield is positioned around the first scintillator. A multi-channel analyzer is operatively connected to the gamma-ray spectrometer and the annular array of individual scintillators. In one embodiment the first scintillator comprises a segmented scintillator. In one embodiment the annular array of individual scintillators comprises an annular array of segmented scintillators.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
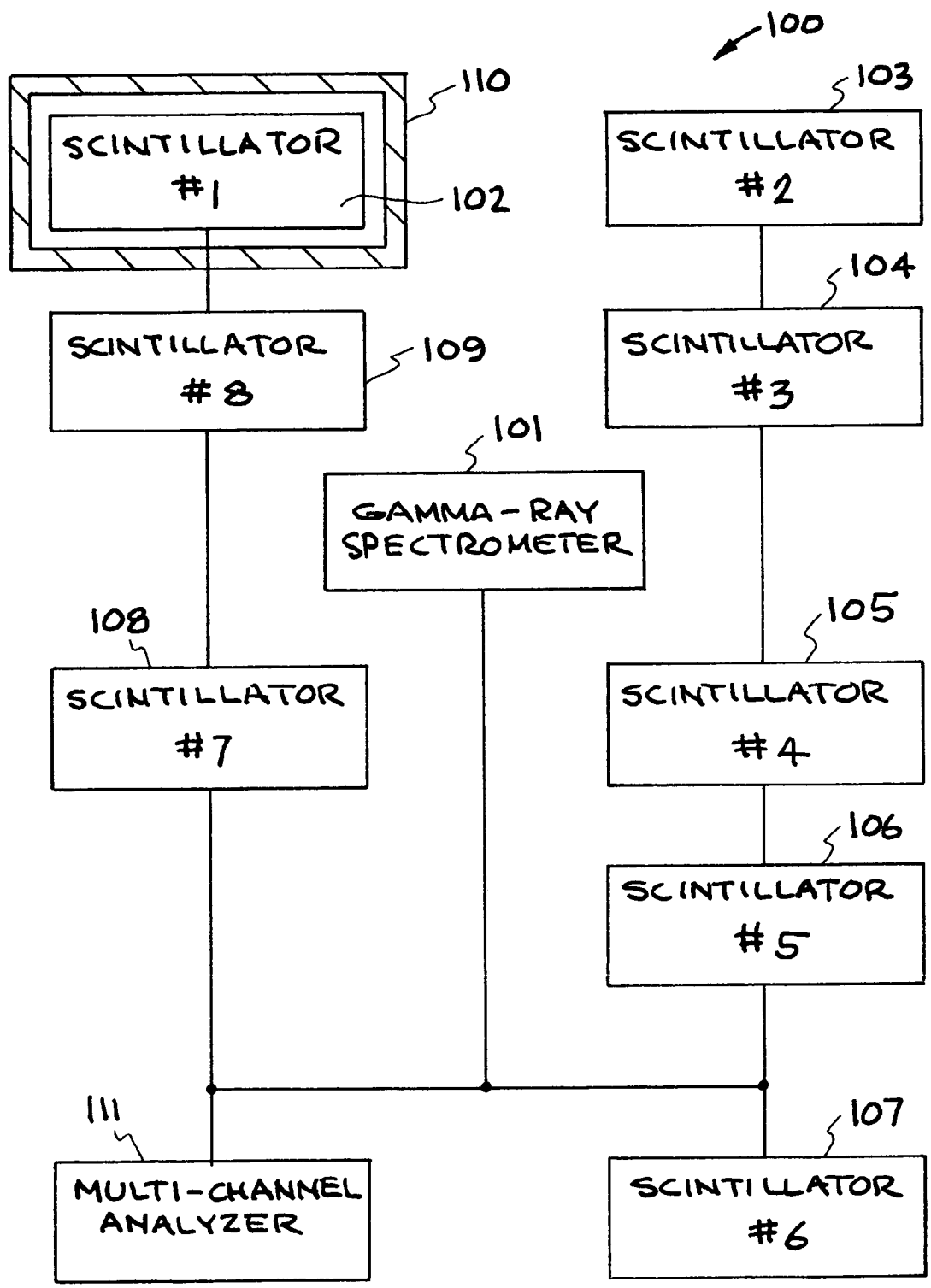
FIG. 1 illustrates and embodiment of a Compton gamma-ray detector constructed in accordance with the present invention.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to the drawings and in particular to FIG. 1, one embodiment of a system of the present invention is illustrated. This embodiment of the system is designated generally by the reference numeral 100. The system 100 provides a streamline Compton scattered gamma-ray detection system that is suitable for field use. The system 100 is made of three main parts, part 1: an annular array of segmented scintillators arrayed around a standard gamma-ray spectrometer, part 2: a radiation shield around number one, and part 3: electronics that interfaced to a multi-channel analyzer.

The first part of the system 100, part 1, includes scintillator #1 designated by the reference numeral 102 and scintillators #2-8 designated by the reference numerals 103 through 109. The scintillators #1-8 designated by the reference numerals 102 through 109 are arrayed around a gamma-ray spectrometer 101.

The second part of the system 100, part 2, includes a radiation shield 110 around scintillator #1, reference numeral 102. The radiation shield is designated by the reference numeral 110.

The third part of the system 100, part 3, includes a multi-channel analyzer 111 operatively connected to the scintillators #1-8 designated by the reference numerals 102 through 109 and the gamma-ray spectrometer 101.

The present invention, as illustrated by the system 100, provides a system that will reject certain gamma-rays based on a coincidence generated by two detectors. Gamma rays coming from all directions at once are tracked as they scatter inside the system 100. The system will detect clandestine nuclear materials. However, the instrument also can be used to detect cancer early by using radiolabeled tracers to target unique molecular characteristics of the disease.

In the system 100, the main detector is HPGe, where its high resolution is desired. The HPGe is the spectroscopy leg (in a three legged architecture). When a gamma does not fully absorb in the Ge, the part of the gamma energy that leaks is captured in the second leg of the system (BGO gamma detector). In the present invention, particular attention is paid to the geometry and features of the second leg to increase the system utility where smaller size is needed and field portability lower weight is needed and to increase the ability to volume manufacturing and deploy.

Figure 2:
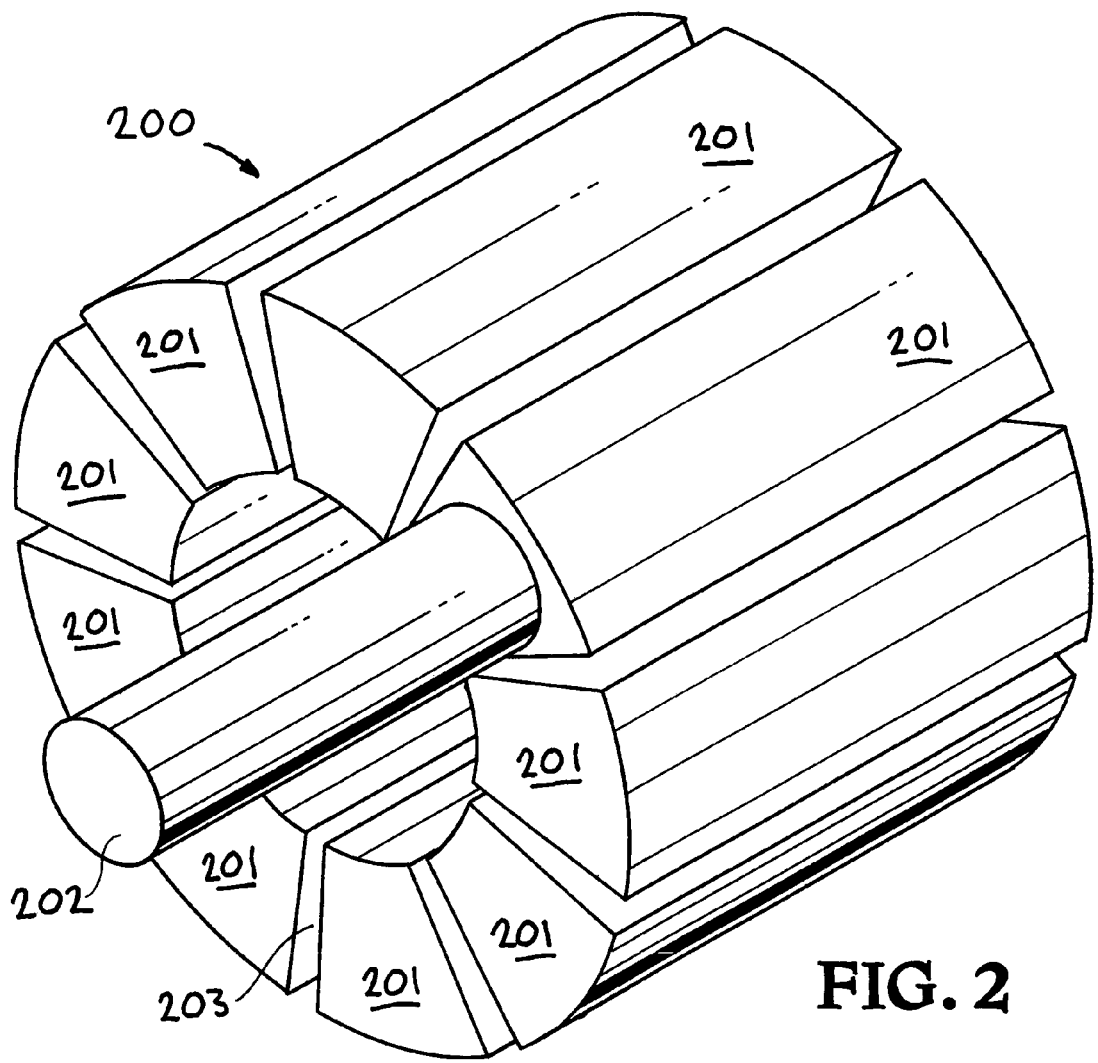
FIG. 2 illustrates another embodiment of a system constructed in accordance with the present invention.

Referring to FIG. 2, another embodiment of a system of the present invention is illustrated. This embodiment of the system is designated generally by the reference numeral 200. The system 200 includes a multiplicity of scintillations 201. The system 200 provides an annular coaxial detector that is segmented axially to improve resolution and light collection.

A round PMT designated by the reference numeral 202 is mounted end-on to view down the BGO wedge 203. Annular/coaxial geometry using the higher density BGO reduces the size (radius) of the parts that must be added to the basic HPGe. This streamlines the system to make it portable, easily no larger than the LN dewar. Realizing that most hpge detectors preferentially accept gamma-rays from the front, and that leakage (lost Compton gammas) radiates in all directions, we accomplish maximum collection efficiency (~3 Pi) by placing the cylindrical annulus close to the sides of the hpge cryostat and make it protrude beyond the ends of the hpge crystal to increase the efficiency of collection of the leaking gamma-rays.

Figure 3:
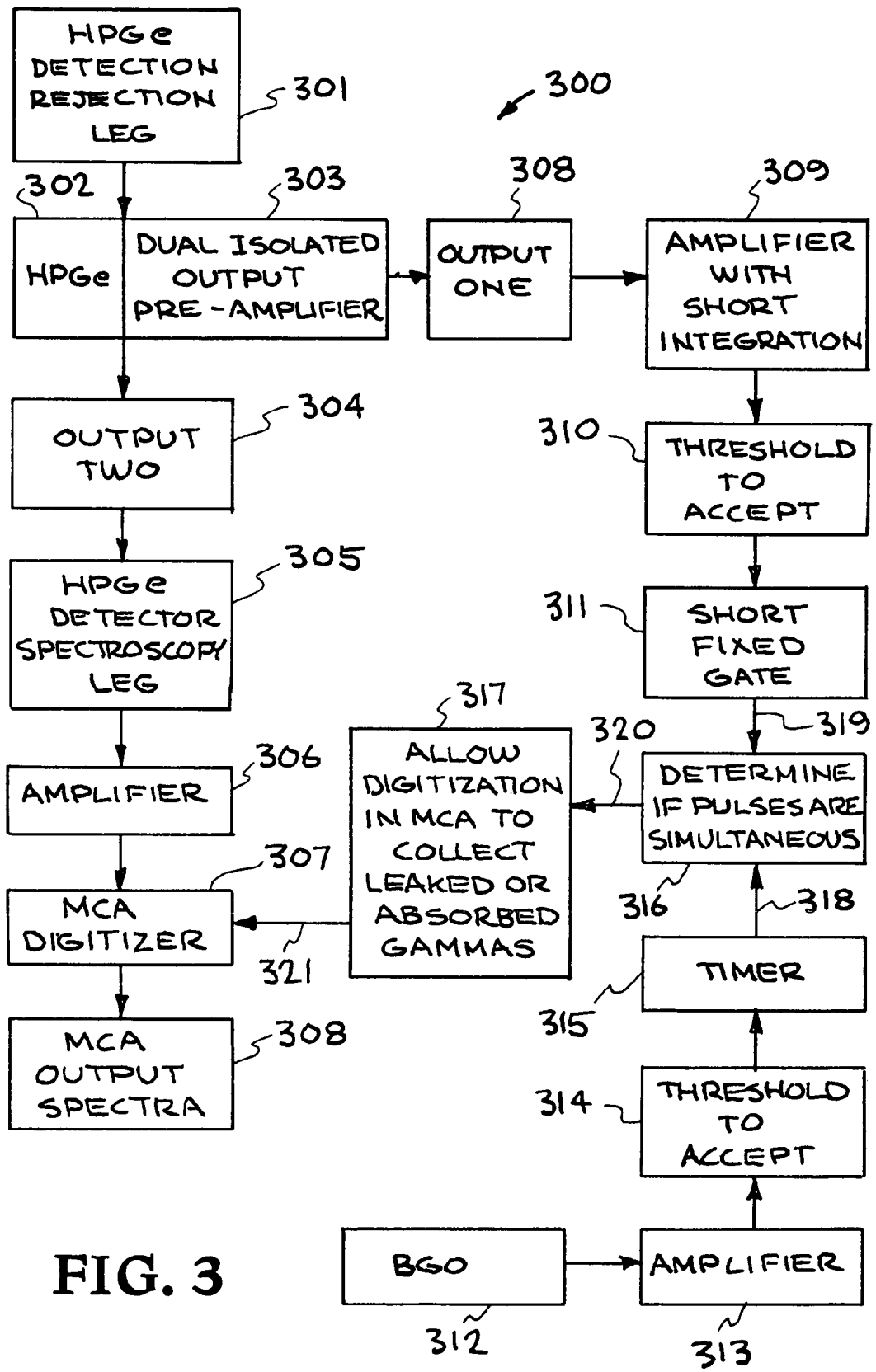
FIG. 3 illustrates yet another embodiment of a system constructed in accordance with the present invention.

Referring to FIG. 3, another embodiment of a system of the present invention is illustrated. This embodiment of the system is designated generally by the reference numeral 300. The system 300 includes the following components: Hepge Detection Rejection Leg 301, HPGe 302, Dual Isolated-Output Pre-amplifier 303, Hpge Detector spectroscopy Leg 305 Amplifier 306, MCA Digitizer 307, MCA Output Spectra 308, Amplifier with Short Integration 309, Threshold to Accept 310, Short Fixed Gate 311, BGO 312, Amplifier 313, Threshold to Accept 314, and Timer 315.

The structural components of the system 300 having been described, the operation of the system 300 will now be considered. The concept of Compton rejection of the present invention, as illustrated by the system 300, is to reject certain gamma-rays based on a coincidence generated by two detectors. The main detector is HPGe 302, where its high resolution is desired. The HPGe is the spectroscopy leg (in a three legged architecture). When a gamma does not fully absorb in the Ge, the part of the gamma energy that leaks is captured in the second leg of the system (BGO gamma detector), n the system 300, particular attention is paid to the geometry and features of the second leg to increase the system utility where smaller size is needed and field portability lower weight is needed and to increase the ability to volume manufacturing and deploy.

The annular coaxial detector is segmented axially to improve resolution and light collection. Annular/coaxial geometry using the higher density BGO reduces the size (radius) of the parts that must be added to the basic HPGe. This streamlines the system to make it portable, easily no larger than the LN dewar. Realizing that most hpge detectors preferentially accept gamma-rays from the front, and that leakage (lost Compton gammas) radiates in all directions, Applicants accomplish maximum collection efficiency (~3 Pi) by placing the cylindrical annulus close to the sides of the hpge cryostat and make it protrude beyond the ends of the hpge crystal to increase the efficiency of collection of the leaking gamma-rays.

Use minimal integration (short time constant e.g. ~3 micro seconds matched to the hpge mca integrate time) to minimize the length of the pulses from the hpge and BGO; each of which will be used in a coincidence gate. This reduces the length of what will become the reject signal. Improve the rejection quality by allowing extension of this "3" microsecond reject signal (also chosen matched the main-leg integration time) if another Compton registers in the BGO. Another aspect of what we do is to make the process of causing the rejection signals to be generated on a time basis shorter than the hpge signal processing time because it does a better job of finding BGO pulses and preventing the mca from catching the tail of a second incomplete gamma deposition immediately after a pulse conversion in the mca. Applicants use the fast edge of the pmt signal as the trigger to extend the gate, on a time scale shorter than any integration time in either leg.

Use a common voltage setting for the BGO and compensate for gain variations by using an adjustable pulse acceptance threshold. This improves the utility in field use since the HV supply in the electronics box may be universally set for all time. Use the second buffered/isolated output (common in HPGe preamps) to reduce gain requirements in this leg. This also improves the performance of the HPGe resolution, relative to a shared HPGe signal since noise is reduced by isolating the proper spectroscopic leg. Collecting both the rejected hpge gamma-rays and the accepted gamma-rays, one may improve rejection further by reading any photopeaks and adding them back to the accepted spectrum.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A portable Compton scattered gamma-ray detector, comprising:
    a gamma-ray spectrometer,
    an annular array of individual scintillators, said scintillators positioned so that they are arrayed around said gamma-ray spectrometer, said annular array of individual scintillators including a first scintillator and a multiplicity of other scintillators,
    a radiation shield surrounding said first scintillator,
    wherein said multiplicity of other scintillators are open without radiation shielding, and
    a multi-channel analyzer operatively connected to said gamma-ray spectrometer and said annular array of individual scintillators.

2. The Compton scattered gamma-ray detector of claim 1 wherein said annular array of individual scintillators comprises an annular array of segmented scintillators.

3. The Compton scattered gamma-ray detector of claim 1 wherein said first scintillator comprises a first segmented scintillator with a radiation shield surrounding said first segmented scintillator and wherein said multiplicity of other scintillators are open without radiation shielding.

4. A portable Compton scattered gamma-ray detector, comprising:
    gamma-ray spectrometer means,
    an annular scintillator means arrayed around said gamma-ray spectrometer means, said annular scintillator means including
    a first scintillator and
    a multiplicity of other scintillators,
    radiation shield means surrounding said first scintillator,
    wherein said multiplicity of other scintillators are open without radiation shielding, and
    multi-channel analyzer means operatively connected to said gamma-ray spectrometer means and said annular scintillator means.

5. The Compton scattered gamma-ray detector of claim 4 wherein said annular scintillator means comprises an annular array of segmented scintillators.

* * * * *